United States Patent [19]
Chen et al.

[11] Patent Number: 5,653,949
[45] Date of Patent: Aug. 5, 1997

[54] CATALYTIC OXIDATION CATALYST AND METHOD FOR CONTROLLING VOC, CO AND HALOGENATED ORGANIC EMISSIONS

[75] Inventors: James M. Chen, Edison; Pascaline H. Nguyen, Morganville, both of N.J.

[73] Assignee: Engelhard Corporation, Iselin, N.J.

[21] Appl. No.: 671,900

[22] Filed: Jun. 28, 1996

Related U.S. Application Data

[63] Continuation of Ser. No. 366,537, Dec. 30, 1994, Pat. No. 5,578,283.

[51] Int. Cl.$^6$ .................................................. C01B 7/00
[52] U.S. Cl. ............................ 423/240 S; 423/240 R; 502/324; 502/325
[58] Field of Search ..................... 423/240 R, 240 S; 502/324, 325

[56] References Cited

U.S. PATENT DOCUMENTS

| | | | |
|---|---|---|---|
| 3,767,453 | 10/1973 | Hoekstra | 117/46 CA |
| 3,785,998 | 1/1974 | Hoekstra | 252/477 R |
| 3,920,583 | 11/1975 | Pugh | 252/465 |
| 3,972,979 | 8/1976 | Kagayama | 423/240 |
| 4,053,557 | 10/1977 | Kagayama | 423/240 |
| 4,059,675 | 11/1977 | Yang et al. | 423/240 |
| 4,059,676 | 11/1977 | Yang et al. | 423/240 |
| 4,059,683 | 11/1977 | Lindberg et al. | 423/481 |
| 4,085,193 | 4/1978 | Nakajima et al. | 423/239 |
| 4,152,246 | 5/1979 | Weisang et al. | 208/139 |
| 4,157,374 | 6/1979 | Carpenter et al. | 423/210 |
| 4,209,496 | 6/1980 | Carpenter et al. | 423/210 |
| 4,299,734 | 11/1981 | Fujitani et al. | 252/462 |
| 4,500,650 | 2/1985 | Wyatt et al. | 502/204 |
| 4,622,311 | 11/1986 | Wakui et al. | 502/235 |
| 4,983,366 | 1/1991 | Deller et al. | 423/240 |
| 5,061,464 | 10/1991 | Cordonna, Jr. et al. | 423/213 |
| 5,139,992 | 8/1992 | Tauster et al. | 502/304 |
| 5,145,825 | 9/1992 | Deeba et al. | 502/242 |
| 5,182,242 | 1/1993 | Marler | 502/66 |
| 5,202,102 | 4/1993 | Nguyen | 423/240 |
| 5,254,797 | 10/1993 | Imoto et al. | 588/207 |
| 5,283,041 | 2/1994 | Nguyen | 423/240 |
| 5,292,496 | 3/1994 | Nagashima et al. | 423/584 |
| 5,294,419 | 3/1994 | Hiraoka et al. | 423/239.1 |

FOREIGN PATENT DOCUMENTS

| | | |
|---|---|---|
| 0174495 | 3/1986 | European Pat. Off. . |
| 0 539 846 | 5/1991 | European Pat. Off. . |
| 0449423 | 10/1991 | European Pat. Off. . |
| 0 488 331 | 3/1992 | European Pat. Off. . |
| 0514682 | 11/1992 | European Pat. Off. . |
| 0547226 | 6/1993 | European Pat. Off. . |
| 2514585 | 10/1976 | Germany . |
| 1064 19/91 | 5/1991 | Japan . |
| 1 485 375 | 8/1977 | United Kingdom . |
| 2059934 | 4/1981 | United Kingdom . |
| 90/13352 | 11/1990 | WIPO . |
| 90/02386 | 11/1990 | WIPO . |
| 92 05861 | 4/1992 | WIPO . |

OTHER PUBLICATIONS

Bond and Sadeghi, "Catalyzed Destruction of Chlorinated Hydrocarbons", J. Appl. Chem. Biotechnology, 25, 241–248 (1975).

Chatterjee and Greene, "Oxidative Catalysis of Chlorinated Hydrocarbons by Metal-Load Acid Catalysts", Journal of Catalysis 130, 76–85 (1991).

Lester, "Catalytic Destruction of Hazardous Halogenated Organic Chemicals", Air & Waste Management Assoc., For Presentation at the 82nd Annual Meeting & Exhibition (Jun. 25–30, 1989).

Melchor, et al. "Physicochemical Properties and Isomerization Activity of Chlorinated $Pt/Al_2O_3$ Catalyst", J. Chem. Soc., Faraday Trans.1 82,3667–3679 (1986).

Murakami, et al. "Structure Sensitive and Insensitive Reactions on Supported Vanadium Oxide Catalysts", Intern. Cong. on Catalysts 7th, pp. 1344–1356 (1980).

Spivy, "Complete Catalytic Oxidation of Volatile Organics", Ind. Eng. Chem. Res. 26, 2165–2180 (1987).

Abstract of EP Application 306540 (Mar. 15, 1989).

Abstract of Japanese Patent Application Assigned to Asahi Chemical Ind. KK, No. J61141919 (Jun. 28, 1986).

Abstract of Japanese Patent Application Assigned to Nissan Motor Co. Ltd, Pub. No. JP63287555 (Nov. 04, 1988).

*Primary Examiner*—Deborah Jones
*Assistant Examiner*—Amy M. Harding

[57] ABSTRACT

A catalyst and process for treating gas streams which contain halogenated organic compounds, non-halogenated organic compounds, carbon monoxide or mixtures thereof, and particularly gas streams which contain organobromides. The catalyst comprises at least one platinum group metal, zirconium oxide and at least one oxide of manganese, cerium or cobalt.

2 Claims, No Drawings

CATALYTIC OXIDATION CATALYST AND METHOD FOR CONTROLLING VOC, CO AND HALOGENATED ORGANIC EMISSIONS

This application is a continuation of copending application Ser. No. 08/366,537 filed Dec. 30, 1994 now issued as U.S. Pat. No. 5,578,283.

BACKGROUND OF THE INVENTION

1. Field of the Invention

This invention relates to a novel catalyst and process for the catalytic oxidation of gaseous carbonaceous emissions, in particular, gaseous carbonaceous emissions that include halogen-containing compounds, and more particularly organobromides.

2. Description of Related Art

The treatment of gaseous emissions containing volatile organic compounds and carbon monoxide has been of increasing concern in recent years. Thermal incineration, catalytic oxidation and adsorption are commonly used for removing these pollutants. Thermal incineration requires high operating temperatures and high capital cost facilities. If the gaseous stream also includes halogenated compounds, thermal incineration can evolve toxic halogenated compounds under certain operating conditions. In some instances, adsorption by adsorbents such as carbon is an alterative. However, this process does not destroy the pollutants, but merely concentrates them. Furthermore, adsorption efficiency can be adversely impacted by fluctuating concentrations of the gaseous components.

Catalytic oxidation is an energy efficient and economical way of destroying gaseous organic emissions. It operates at significantly lower temperatures and shorter residence time than thermal incineration and requires smaller reactors made of less expensive materials.

Methods for the catalytic oxidation of non-halogenated organic and halogenated organic compounds are well known in the art. For example, in the article by G. C. Bond and N. Sadeghi, "Catalyzed Destruction of Chlorinated Hydrocarbons" *J. Appl. Chem. Biotechnol.*, 1975, 25, 241–248, it is reported that chlorinated hydrocarbons are converted to HCl and $CO_2$ over platinum on gamma alumina catalyst.

U.S. Pat. Nos. 3,972,979 and 4,053,557 describe the decomposition of halogenated hydrocarbons by oxidation over chromium oxide or a boehmite supported platinum.

U.S. Pat. Nos. 4,059,675, 4,059,676 and 4,059,683 describe methods for decomposing halogenated organic compounds using catalysts containing ruthenium, ruthenium-platinum and platinum, respectively, in the presence of an oxidizing agent at a temperature of at least 350° C.

The article by James J. Spivy, "Complete Catalytic Oxidation of Volatile Organics", *Ind. Eng. Chem. Res.*, 1987, 26, 2165–2180, is a review of the literature dealing with the heterogeneous catalytic oxidation of volatile organic compounds.

The article by S. Chatterjee and H. L. Green, "Oxidative Catalysis by Chlorinated Hydrocarbons by Metal-Load Acid Catalysts", *Journal of Catalysis*, 1991, 130, 76–85, reports on a study of the catalytic oxidation of methylene chloride in air using supported zeolite catalysts H—Y, Cr—Y, and Ce—Y.

The article by A. Melchor, E. Garbowski, M. V. Michel-Vital Mathia and M. Primer, "Physicochemical Properties and Isomerization Activity of Chlorinated $Pt/Al_2O_3$ Catalyst", *J. Chem Soc., Faraday Trans.* 1, 1986, 82, 3667–3679, reports that chlorination of alumina leads to a very acidic solid because of an enhancement of the strength and the number of strong Lewis Sites. The chlorination treatment enhances the sintering of platinum.

U.S. Pat. No. 4,983,366 describes a method for the catalytic conversion of waste gases containing hydrocarbons and carbon monoxide by passing the waste gases through a first zone containing a catalyst such as aluminum oxide, silicon dioxide, aluminum silicate and/or a zeolite optionally containing oxidic compounds or barium, manganese, copper, chromium, and nickel, and then through a second zone containing a catalyst such as platinum and/or platinum and/or palladium or platinum and rhodium.

PCT International Application No. PCT/US90/02386 describes a catalytic process for converting or destroying organic compounds including organohalogen compounds using a catalyst which contains as a catalytic component titania. The preferred catalyst also contains vanadium oxide, tungsten oxide, tin oxide; and at least one noble metal selected from the group consisting of platinum, palladium, and rhodium characterized in that the vanadium oxide, tungsten oxide and noble metals are uniformly dispersed on the titania.

U.S. Pat. No. 5,283,041 (commonly assigned to assignee of the instant invention), hereby incorporated by reference, discloses an oxidation catalyst for treating a gas stream containing compounds selected from the group consisting of halogenated organic compounds, other organic compounds and mixtures thereof. The catalyst comprises a core material of zirconium oxide and one or more oxides of manganese, cerium or cobalt with vanadium oxide dispersed thereon, and may further include a platinum group metal dispersed on the core material.

There is still a need for catalysts for the oxidative destruction of halogenated organic compounds, non-halogenated and carbon monoxide to provide enhanced operating efficiencies at lower operating temperatures. This is particularly true for the treatment of gas streams containing organobromides, which have been found to be particularly difficult to incinerate.

SUMMARY OF THE INVENTION

This invention relates to catalysts and processes for treating gas streams which contain compounds selected from the group consisting of halogenated organic compounds, non-halogenated organic compounds, carbon monoxide and mixtures thereof. The catalysts and processes are particularly suitable for treating gas streams which further contain one or more elemental halogens, specifically including gas streams in which such elemental halogens are initially present or form during the catalytic treatment of halogenated organic compounds. In particular embodiments, the gas streams contain brominated organic compounds and elemental bromine is either initially present or forms during the catalytic treatment.

One embodiment of this invention is a catalyst for treating a gas stream which contains compounds selected from the group consisting of halogen-containing compounds, non-halogenated organic compounds, carbon monoxide (CO) and mixtures thereof. The catalyst useful in the practice of this invention comprises one or more platinum group metals, zirconium oxide and at least one oxide selected from the group consisting of manganese oxide, cerium oxide and cobalt oxide.

Another embodiment of this invention is a process for treating a gas stream which contains compounds selected from the group consisting of halogen-containing compounds, non-halogenated organic compounds, carbon monoxide and mixtures thereof. The process comprises contacting such a gas stream at a temperature from about 150° C. to 550° C. with a catalyst comprising one or more platinum group metals, zirconium oxide and at least one oxide selected from the group consisting of manganese oxide, cerium oxide and cobalt oxide in the presence of an effective amount of oxygen to facilitate oxidation reactions.

In particular embodiments of the catalyst and process of this invention, the gas stream contains halogens in elemental form, such as $Br_2$ or $Cl_2$, or contains halogenated organic compounds which form such elemental halogens during the catalytic treatment. The catalyst and process are particularly suitable for use with gas streams in which the elemental halogen or halogen of the halogenated compound is bromine.

In a particular process of the present invention, a gas stream which contains a brominated organic compound, which may be in combination with non-brominated organic compounds, carbon monoxide or mixtures thereof, is treated with a catalyst comprising at least one platinum group metal, zirconium oxide and manganese oxide. In this process, at least some of the bromine in the brominated organic compounds is converted to elemental bromine. Generally, this catalytic oxidation process converts these compounds of the gas stream to a mixture comprising $CO_2$, bromine, hydrogen bromide and $H_2O$.

The catalyst and process of the present invention are particularly suitable for treating a gas stream which contains one or more elemental halogens, or which contains one or more halogen-containing organic compounds which form elemental halogens during the catalytic oxidation process. When halogen-containing organic compounds are oxidized over catalysts elemental halogen ($X_2$) and hydrogen halide (HX) are formed. Elemental halogen has been found to have a poisoning effect on previously known catalysts, thus reducing the activity of such catalysts. In order to overcome this problem, gas treatments were conducted under conditions to minimize the production of elemental halogen, or were conducted at relatively high temperatures to reduce the effect on the catalyst.

When the halogen in the gas feed is chlorine or fluorine, it has generally been possible to reduce the amount of elemental halogen in the resultant gas to less than 3 weight percent of the total of the halogen-containing compounds ($X_2$ and HX) present by adjusting the amount of available hydrogen in the feed stream. This is generally done by adding enough water to provide the hydrogen for reaction.

However, when the halogen in the halogen-containing organic compound is bromine, it has been found that the formation of $Br_2$ cannot be readily controlled by the injection of water. Thus, when the halogen is bromine, the resultant gas stream generally contains a significant portion of the bromine in elemental form. That is, well above 3 weight percent, and often over 80 weight percent of the bromine in the resultant gas is in the form of $Br_2$ rather than HBr. It has therefore not been possible to overcome the poisoning problem of $Br_2$ by adjusting the feed gas composition. As a result, such bromine containing catalysis reactions have had to be conducted at elevated temperatures, resulting in various problems, such as higher energy costs.

The catalysts of the present invention have been found to be resistant to such elemental halogen poisoning, and thus to be particularly suitable for use when the halogen is bromine. The present catalysts are also particularly suitable for use with any halogen containing gas stream in which the product stream contains more than 3 weight percent of its halogen in elemental form. Thus, chlorine-containing gas streams can be reacted over the present catalysts without the need to add excess hydrogen or water to maintain the $Cl_2$ level below 3 percent. This can result in significant cost savings and ease of operation in treating such chlorine containing streams.

Another characteristic of the catalysts of the present invention is that they were found to remain stable at temperatures of up to 550° C.–600° C., and even higher, without deactivation. Thus, regeneration of the present catalysts by thermal activation can be conducted at relatively higher temperatures, such as 500° C.–550° C., thus allowing such regenerations to be conducted faster and more efficiently than for some previously known catalysts.

The problem of elemental halogen poisoning has particularly been found to occur in catalysts which contain vanadium oxide. It is believed that the elemental halogen is reactive with vanadium oxide, and can thus poison such catalysts. Therefore, in a preferred embodiment of the present invention, the catalyst is substantially free of vanadium. Although vanadium is not a desirable component of the present catalyst, it is to be understood that the presence of an incidental amount of vanadium should not have any significant impact on the effectiveness of the catalyst. Therefore although the catalyst is preferably free of any detectable level of vanadium, the catalyst should still be considered "substantially free of vanadium" as long as it contains less than 0.1 weight percent vanadium (as $V_2O_5$).

DESCRIPTION OF THE PREFERRED EMBODIMENT

As previously stated, this invention provides catalysts and processes for using such catalysts to treat gas streams which contain compounds selected from the group consisting of halogenated organic compounds, non-halogenated organic compounds, carbon monoxide and mixtures thereof. The catalysts and processes are particularly suitable for treating gas streams which further contain one or more molecular halogens, or gas streams in which such molecular halogens form during the catalytic treatment, and more particularly to gas streams which include bromine.

The catalyst of this invention comprises one or more platinum group metals, zirconium oxide and at least one of manganese oxide, cerium oxide or cobalt oxide. The platinum group metals as used herein are platinum, palladium and rhodium.

When reference is made herein to metal oxide(s) or oxide(s) of a metal, it is intended to include all oxide forms of such metal and mixtures thereof as well as hydroxo-oxides, hydrous oxides and the like.

Typically, the catalysts of this invention contain from about 40 up to about 88 weight percent zirconium oxide (as $ZrO_2$), preferably from about 60 up to about 85 weight percent; and from about 3 up to about 48 weight percent of one or more oxides of manganese, cerium or cobalt, preferably about 10 up to about 30 weight percent.

Good results are obtained when the platinum group metal is present in the catalyst in an amount of from about 0.01 to about 8 weight percent of the catalyst, and particularly in an amount of at least about 0.1 weight percent.

In a preferred embodiment, the catalyst is characterized by a core material comprising zirconium oxide and one or more oxides of manganese, cerium or cobalt with a platinum group component dispersed on this core material. The preferred platinum group metal is platinum.

Typically, the core material of this invention contains up to about 90 weight percent zirconium oxide ($ZrO_2$), preferably from about 50 up to about 80 weight percent.

In the case of a core material comprising manganese oxide and zirconium oxide, it is desirable that manganese be present in the core material in an amount up to about 50 weight percent (as $Mn_2O_3$); typically containing at least about 10 weight percent manganese oxide, and preferably from about 15 up to about 35 weight percent.

In the case of a core material comprising cerium oxide and zirconium oxide, it is desirable that cerium oxide be present in the core material in an amount up to about 50 weight percent (as $CeO_2$); typically containing at least about 14 weight percent cerium oxide, and preferably from about 15 up to about 25 weight percent.

In the case of a core material comprising cobalt oxide and zirconium oxide, it is desirable that cobalt oxide be present in the core material in an amount up to about 50 weight percent (as $Co_3O_4$); typically containing at least about 10 weight percent, and preferably from about 15 up to about 35 weight percent.

The core material may be combined with other materials such as binders or adhesion aids or active components such as titania and/or alumina. The core material my be prepared by means well known to those of ordinary skill in the art and include physical mixtures, cogellation, coprecipitation or impregnation. The preferred techniques for preparing the core material of this invention are cogellation and coprecipitation. For further details of these methods see U.S. Pat. No. 4,085,193 which is incorporated by reference for its teaching of techniques for coprecipitation and cogellation. Impregnation may be used in a manner analogous to the methods discussed with regard to dispersing platinum group metals and other components on the core material.

For example, a core material of zirconium oxide and manganese oxide may be prepared by mixing aqueous solutions of a suitable zirconium oxide precursor such as zirconium oxynitrate, zirconium acetate, zirconium oxychloride, or zirconium oxysulfate and a suitable manganese oxide precursor Such as manganese nitrate, manganese acetate, manganese dichloride or manganese dibromide, adding a sufficient amount of a base such as ammonium hydroxide to obtain a pH of 8–9, filtering the resulting precipitate, washing with water, drying at 120°–150° C. and then calcining at 450°–500° C.

A similar procedure employing a soluble cerium or cobalt compound such as cerium nitrate, cerium acetate, cerium sulfate or cerium chloride, cobalt nitrate, cobalt chloride or cobalt bromide may be used if a core material comprising zirconium oxide and oxides of cerium or cobalt is desired.

It is desirable that the core material and the catalyst of this invention have a surface area of from about 25 m²/g to about 275 m²/g, preferably from about 50 up to about 250 m²/g.

The platinum group metals can be dispersed onto the core material by means well known in the art. Impregnation is the preferred method. Impregnation may be carried out by techniques well known to those of ordinary skill in the art.

The metal may be dispersed onto the core material by impregnating the material with a solution containing a compound of the desired platinum group metal(s). The solution may be an aqueous or non-aqueous (organic solvent) solution. Any platinum group metal compound may be used provided the compound is soluble in the chosen solvent and decomposes to the metal upon heating in air at elevated temperatures. Illustrative of these platinum group metal compounds are chloroplatinic acid, ammonium chloroplatinate, bromoplatinic acid, platinum tetrachloride hydrate, platinum dichlorocarbonyl dichloride, dinitrodiamino platinum, amine solubilized platinum hydroxide, rhodium trichloride, hexaamminerhodium chloride, rhodium carbonylchloride, rhodium trichloride hydrate, rhodium nitrate, rhodium acetate, chloropalladic acid, palladium chloride, palladium nitrate, diamminepalladiumhydroxide and tetraamminepalladium chloride.

The impregnation of the particulates or powder with the metal compound solution may be carried out in ways well known in the art. One convenient method is to place the core material in particulate form, e.g., granules, into a rotary evaporator which is partially immersed in a heating bath. The impregnating solution which contains an amount of the desired metal compound to provide the desired concentration of oxide or metal in the finished catalyst is now added to the core material and the mixture cold rolled (no heat) for a time from about 10 to 60 minutes. Next, heat is applied and the solvent is evaporated. This usually takes from about 1 to about 4 hours. Finally, the solid is removed from the rotary evaporator and calcined in air at a temperature of about 400° C.–600° C. for about 1 to 3 hours. If more than one other component is desired, they may be impregnated simultaneously or sequentially in any order.

Alternatively, the core material in powder form is placed into a planetary mixer and the impregnating solution is added under continuous agitation until a state of incipient wetness is achieved. The powder is then dried in an oven for 4–8 hours and calcined at about 400° C.–600° C. for about 1–3 hours.

Other methods of dispersing these oxides onto core material are coprecipitation or cogellation.

The catalyst of the instant invention may be used in any configuration, shape or size which exposes it to the gas to be treated. For example, the catalyst can be conveniently employed in particulate form or the catalyst can be deposited onto a solid monolithic carrier. When the particulate form is desired, the catalyst can be formed into shapes such as tablets, pellets, granules, rings, spheres, etc. The particulate form is especially desirable where large volumes of catalysts are needed, and for use in circumstances in which frequent replacement of the catalyst may be desired. In circumstances in which less mass is desirable or in which movement or agitation of particles of catalyst may result in attrition, dusting and resulting loss of dispersed metals or oxides or undue increase in pressure drop across the particles due to high gas flows, a monolithic form is preferred.

In the employment of a monolithic form, it is usually most convenient to employ the catalyst as a thin film or coating deposited on an inert carrier material which provides the structural support for the catalyst. The inert carrier material can be any refractory material such as ceramic or metallic materials. It is desirable that the carrier material be unreactive with the catalytic components and not be degraded by the gas to which it is exposed. Examples of suitable ceramic materials include sillimanite, petalite, cordierite, mullite, zircon, zircon mullite, spodumene, aluminatitanate, etc. Additionally, metallic materials which are within the scope of this invention include metals and alloys as disclosed in U.S. Pat. No. 3,920,583 (incorporated herein by reference) which are oxidation resistant and are otherwise capable of withstanding high temperatures. For the treatment of gases containing halocarbons, ceramic materials are preferred.

The monolithic carrier material can best be utilized in any rigid unitary configuration which provides a plurality of pores or channels extending in the direction of gas flow. It is preferred that the configuration be a honeycomb configuration. The honeycomb structure can be used advantageously in either unitary form, or as an arrangement of multiple modules. The honeycomb structure is usually oriented such that gas flow is generally in the same direction as the cells or channels of the honeycomb structure. For a more detailed discussion of monolithic structures, refer to U.S. Pat. Nos. 3,785,998 and 3,767,453, which are incorporated herein by reference.

If particulate form is desired, the catalyst can be formed into granules, spheres or extrudates by means well known in the industry. For example, the catalyst powder can be combined with a binder such as a clay and rolled in a disk pelletizing apparatus to give catalyst spheres. The amount of binder can vary considerably but for convenience is present from about 10 to about 30 weight percent.

If a monolithic form is desired, the catalyst of this invention can be deposited onto the monolithic honeycomb carrier by conventional means. For example, a slurry can be prepared by means known in the art such as combining the appropriate amounts of the catalyst of this invention in powder form, with water. The resultant slurry is ball-milled for about 8 to 18 hours to form a usable slurry. Other types of mills such as impact mills can be used to reduce the milling time to about 1–4 hours. This slurry can now be used to deposit a thin film or coating of catalyst of this invention onto the monolithic carrier by means well known in the art. Optionally, an adhesion aid such as alumina, silica, zirconium silicate, aluminum silicates or zirconium acetate can be added in the form of an aqueous slurry or solution. A common method involves dipping the monolithic carrier into said slurry, blowing out the excess slurry, drying and calcining in air at a temperature of about 450° C. to about 600° C. for about 1 to about 4 hours. This procedure can be repeated until the desired amount of catalyst of this invention is deposited on said monolithic honeycomb carrier. It is desirable that the catalyst of this invention be present on the monolithic carrier in an amount in the range of about 1–4 g of catalyst per $in^3$ of carrier volume and preferably from about 1.5–3 $g/in^3$.

An alternative method of preparation is to disperse the platinum group metal component onto a core material coated monolith in an analogous way to that previously described. That is, the monolithic honeycomb carrier which has dispersed thereon core material and other optional components can be dipped into an aqueous solution containing a soluble and decomposable noble metal compound, dried and calcined at a temperature of 400° to 500° C. for about 1 to about 5 hours. Any decomposable platinum group metal compound as enumerated above may be used. The concentration of the platinum group metals are also as stated above.

Another embodiment of this invention is a process for destroying or converting by oxidation and/or hydrolysis halogenated organic compounds (also referred to herein as organohalogen compounds) and other organic compounds present in a gas stream comprising contacting the gas stream at a temperature of about 175° C. to about 550° C. and preferably at a temperature of about 250° C. to about 475° C. with the catalyst described heretofore. The organohalogen compounds which may be treated are any organic compounds which contain at least one halogen atom in the structure of the compounds. Some specific examples are chlorobenzene, dichlorobenzenes, fluorobenzene, carbon tetrachloride, chloroform, methyl chloride, vinyl chloride, methylene chloride, ethyl chloride, ethylene chloride, ethylidene dichloride, 1,1,2-trichloroethane, 1,1,1-trichloroethane, methyl bromide, ethylene dibromide, trichloroethylene, tetrachloroethylene, polychlorinated biphenyls, chlorotrifluoromethane, dichlorodifluoromethane, 1-chlorobutane, ethyl bromide, dichlorofluoromethane, chloroformic acid, trichloroacetic acid and trifluoroacetic acid. The process of this invention may also treat a gas stream which contains other organic compounds which do not contain any halogens in their structure. These other organic compounds include hydrocarbons, oxygenates, amines, etc. Specific examples include benzene, toluene, xylenes, phenol, ethyl alcohol, methyl acetate, methyl formate isopropyl amine, butyl phthalate, aniline, formaldehyde, methyl ethyl ketone, acetone, etc.

Many gas streams already contain enough oxygen ($O_2$) to oxidize all the pollutants, and most gas streams contain a large excess. In general, a large excess of oxygen greatly facilitates the oxidation reaction. In the event that the gas stream does not contain enough oxygen, oxygen, preferably as air, may be injected into the gas stream prior to contact with the catalyst. The minimum amount of oxygen which must be present in the gas stream is the stoichiometric amount necessary to convert the carbon and hydrogen in the compounds present to carbon dioxide and water. For convenience and to insure that the oxidation reaction goes to completion, it is desirable that an excess of oxygen be present. Accordingly, it is preferable that at least two times the stoichiometric amount and most preferably at least five times the stoichiometric amount of oxygen be present in the waste gas stream.

It is also understood that the process of the present invention is not dependent on the concentration of the organic compounds and/or the organohalogen compounds. Thus, gas streams with a very wide concentration range of pollutants can be treated by the instant process. The process of this invention is also applicable to processes wherein liquid organohalogen compounds and organic compounds are vaporized and mixed with oxygen.

The invention has been found to be particularly useful in treating vent gases derived from industrial processes that make phthalic acid compounds such as terephthalic acid (TPA), purified terephthalic acid, isophthalic acid (IPA) and alizarinic acid from xylene via catalytic reactions that use bromine as an initiator. Similarly, trimellitic anhydride is made by catalytic processes from trimethylbenzene using bromine as initiator. Further, catalyzed reactions making dicarboxylic acids from dimethyl naphthalene also use bromine. The desired acid end-product of these reactions typically are recovered by condensation, leaving a vent gas waste stream comprised of various volatile organic compounds, such as toluene, xylene, benzene, methyl formate, acetic acid, alcohol, carbon monoxide and methyl bromide. Compared with conventional catalytic control, the processes and catalysts of this invention provide the advantage of effective catalytic oxidation of the vent gas constituents at reduced operating temperatures and/or catalyst volume.

Another application of the invention involves treatment of volatile organic compounds and halogenated organic compounds, particularly chlorinated organic compounds such as chloroform and dioxin, derived from chlorine bleaching of pulp.

The requirement of the catalyst bed volume for a given application is normally referred to as volume hourly space velocity (VHSV), which is defined as the ratio of gaseous hourly flow rate to the catalyst bed volume. In the practice of this invention, the volume hourly space velocity (VHSV) can vary substantially preferably from about 1,000 to about 100,000 $h^{-1}$ and more preferably from about 5,000 to about 50,000 $h^{-1}$ based on gas rates calculated at standard temperature and pressure. For a fixed flow rate, the VHSV can be controlled by adjusting the size of the catalyst bed.

Once the gas stream has been contacted with the catalyst and the pollutants destroyed, the catalyst treated gas stream may be further treated, if desired, to remove the halogen acid and any halogens which are formed during the conversion process. For example, the treated gas stream may be passed through a scrubber to absorb the acid. The scrubber may contain a base such as sodium or ammonium hydroxide which neutralizes the acids and solubilizes the halogens as basic hypohalites and halides.

This invention is exemplified in the following examples. Of course, these examples are not intended as limiting this invention, as modification of the examples by ordinary expedient will be readily apparent to those of ordinary skills in the art.

EXAMPLE 1

Tests were conducted to demonstrate that the high stability and activity of the catalysts of this invention. A catalyst was prepared comprising a monolithic cordierite honeycomb carrier coated with manganese oxide and zirconia on which platinum was dispersed. The catalyst was aged in a test gas stream containing 50–100 ppm methyl bromide at 10,000 $h^{-1}$ VHSV at 450° C. for 200 hours. After this aging, the catalyst still destroyed more than 99% of the methyl bromide in a test stream containing 50–100 ppm methyl bromide at 20,000 $h^{-1}$ VHSV at 350° C.

EXAMPLE 2

A mixture of a 20% solution of zirconyl oxynitrate (790 g) and a 50% manganese nitrate solution (100 g) is prepared. A 7M solution of ammonium hydroxide is added to this mixture with constant stirring to obtain a pH of 3.5 and gel formation. One liter of water is added to the gel and the gel is broken by stirring with a large spatula. A 7M ammonium hydroxide solution is added to obtain a pH of 8–9. This mixture is then filtered and washed with additional water. The resulting powder is dried at 120° C. overnight and then calcined at 500° C. for two hours to yield a coprecipitated manganese oxide/zirconia powder.

EXAMPLE 3

The manganese oxide/zirconia catalyst prepared in Example 2 is impregnated with 80 g of an aqueous amine-solubilized platinum hydroxide ($H_2Pt(OH)_6$) solution (15.1% Pt) and 69.7 g of water. The powder is then dried at 120° C. overnight and calcined at 500° C. for one hour. A cordierite honeycomb of 3 inches in length and 400 cells per square inch is coated by dipping into the slurry. After dipping, the excess slurry is blown out with an air gun. The sample is dried at 120° C. for 1 hour, and calcined at 500° C. for 1 hour. This procedure is repeated until the monolith has a 1.5 g/$in^3$ catalyst loading.

EXAMPLE 4

A platinum on cerium oxide/zirconia powder is prepared in the same manner as the platinum on manganese oxide/zirconia catalyst described in Example 3, employing 800 g ceria/zirconia (20% $CeO_2$) and impregnated with 80 g of an aqueous amine-solubilized platinum hydroxide ($H_2Pt(OH)_6$) solution (15.1% Pt) and 69.7 g of water. The powder of this example is applied to the honeycomb without the alumina adhesion aid.

EXAMPLE 5

A mixture of a 20% solution of zirconyl oxynitrate (790 g), a 50% solution of manganese nitrate (100 g) and 81.32 g of cobalt nitrate is prepared. A 7M solution of ammonium hydroxide is added to this mixture with constant stirring to obtain a pH of 3.5 and gel formation. One liter of water is added to the gel and the gel is broken by stirring with a spatula. A 7M ammonium hydroxide solution is added to obtain a pH of 8–9. This mixture is filtered and washed with additional water. The resulting powder is dried at 120° C. overnight and then calcined at 500° C. for two hours to yield the desired cobalt oxide/manganese oxide/zirconia powder. This powder is then impregnated with platinum in the same manner as described in Example 3.

EXAMPLE 6

A test generally used to evaluate catalyst efficiency for the destruction of halogenated organics and other organic compounds uses a quartz tube reactor with a diameter of 1 inch placed inside a Lindberg furnace. The gases are introduced from the top of the tube and flow downward over the catalyst. Catalyst on a honeycomb monolith having a ⅞-inch diameter and 1-inch length is placed in the middle of the tube and the destruction of organic compounds by the catalyst is evaluated. The catalyst is tested at temperatures ranging from 175° C. to 450° C.

The feed gas contained 50 ppm methyl bromide, 10 ppm toluene, 10 ppm benzene, 7000 ppm CO, 3% $O_2$ and 2.5% $H_2O$. After aging at 450° C. in this stream for 176 hours, the conversions of these organic species and CO were measured at 30,000 $h^{-1}$ VHSV. A hydrocarbon analyzer (FID) and a gas chromatograph were used to analyze the compositions in the inlet and outlet gas samples.

The conversion efficiency is calculated at various temperatures using equation 1:

$$\% \text{ conversion} = [(C_{in} - C_{out})/C_{in}] \times 100 \quad (1)$$

where $C_{in}$ is the inlet concentration of the organic compound to be converted and $C_{out}$ is the outlet concentration.

The results of the foregoing tests are shown in the following table to exemplify the high destruction efficiencies for halogenated organics and other organics using the catalysts of this invention.

TABLE 1

| Temperature (°C.) | Destruction Efficiency (%) | | | |
|---|---|---|---|---|
| | CO | Toluene | Benzene | Methyl Bromide |
| 250 | 50 | 40 | 20 | 28 |
| 300 | 90 | 85 | 30 | 78 |
| 350 | 99+ | 99+ | 95 | 99+ |
| 400 | 99+ | 99+ | 99+ | 99+ |

What is claimed is:

1. A process for treating a gas stream which contains at least one brominated organic compound, the process comprising contacting said gas stream with a catalyst comprising at least one platinum group metal, zirconium oxide and manganese oxide, and wherein the catalyst is substantially free of vanadium.

2. The process of claim 1 wherein said gas stream further comprises non-brominated organic compounds, carbon monoxide or mixtures thereof.

* * * * *